(12) United States Patent
Semin et al.

(10) Patent No.: US 11,730,972 B2
(45) Date of Patent: Aug. 22, 2023

(54) DEVICE FOR MAGNETIC STIMULATION

(71) Applicant: VRTX Technologies OU, Tallinn (EE)

(72) Inventors: Andrei V. Semin, Murom (RU); Andrei L. Vislenko, Saint-Petersburg (RU); Andrei L. Kotikov, Saint-Petersburg (RU); Pavel A. Sergushin, Saint-Petersburg (RU); Timur R. Shamsi, Saint-Petersburg (RU); Taras I. Vilkhovyi, Saint-Petersburg (RU); Vladimir A. Proskurov, Toronto (CA); Miguel Antonio Lopez Hurtado-Zaragoza, El Paso, TX (US); Joanna Alfano, Toronto (CA)

(73) Assignee: VRTX TECHNOLOGIES OU, Tallinn (EE)

( * ) Notice: Subject to any disclaimer, the term of this patent is extended or adjusted under 35 U.S.C. 154(b) by 0 days.

(21) Appl. No.: 17/598,279

(22) PCT Filed: Jun. 8, 2020

(86) PCT No.: PCT/IB2020/055357
§ 371 (c)(1),
(2) Date: Sep. 26, 2021

(87) PCT Pub. No.: WO2021/001707
PCT Pub. Date: Jan. 7, 2021

(65) Prior Publication Data
US 2022/0176145 A1 Jun. 9, 2022

(30) Foreign Application Priority Data

Jun. 30, 2019 (RU) .......................... RU2019120363

(51) Int. Cl.
*A61N 2/02* (2006.01)
*A61N 2/00* (2006.01)

(52) U.S. Cl.
CPC ................ *A61N 2/02* (2013.01); *A61N 2/006* (2013.01); *A61N 2/008* (2013.01)

(58) Field of Classification Search
CPC ............ A61N 1/36062; A61N 1/36071; A61N 1/36171; A61N 2/006; A61N 2/008; A61N 2/02
See application file for complete search history.

*Primary Examiner* — Christine H Matthews
(74) *Attorney, Agent, or Firm* — Patentagar PLLC; Alexander Rabinovich

(57) ABSTRACT

Disclosed is a device for magnetic action on living bodies to perform physiotherapy or stimulating effects on the tissues and internal organs of a human being or an animal to eliminate pain syndromes, stimulate the processes of vital activity and regeneration, and accelerate tissue recovery after invasive effects and injuries. The device comprises an oscillator connected to an inductor including a bifilar coil made as a flat disk. Two coil windings formed as concentrically arranged spirals of adjacent wires of different windings are placed on a dielectric substrate. When attached to the skin surface, the device allows to purposefully target pathogenic areas and organs located at 3-6 cm under the surface, while practically not affecting the tissues located near that surface. Suitable for clinical or home application, the device can be used for relieving pain of various etiologies, treating menstrual syndrome, hemorrhoids, joint diseases, healing injuries, and stimulating cell proliferation.

9 Claims, 7 Drawing Sheets

DEVICE FOR MAGNETIC STIMULATION

CROSS-REFERENCE TO RELATED APPLICATIONS

The present application claims priority from application PCT/IB2020/055337 filed 8 Jun. 2020, which, in turn, claims priority from Russian application 2019120363 filed 30 Jun. 2019, both applications being hereby incorporated by reference in their entirety.

BACKGROUND OF THE INVENTION

1. Field of the Invention

The invention relates to devices and instruments for magnetic effect, which can be applied in medicine and veterinary medicine to perform magnetic physiotherapeutic or magnetic stimulating effect on tissues and internal organs of a human being or an animal in order to eliminate pain syndromes, stimulate vital processes and regeneration, accelerate the restoration of human and animal tissues after invasive influences and injuries.

Magnetic stimulation is one of the most promising methods of magnetic impact on tissues and internal organs of a human being. Magnetic stimulation in various amplitude-frequency ranges has proven to be effective in prevention and treatment of central nervous system diseases, wounds, and bone fractures healing, as well as functional recovery of sensory systems.

Magnetic therapy is a non-invasive, safe, and easy-to-use method for pain management, treatment of inflammation, injuries and other diseases and abnormalities. Magnetic fields cause orientation and concentration changes of biologically active macromolecules, thus affecting the kinetics of biochemical reactions and the speed of biophysical processes in the body. The field can affect macromolecules not only directly, but also through its influence on the environment of these molecules. The primary effect of fields on the body includes an orientation rearrangement of cell membranes that build the cell wall and form the basis of intracellular structures. This affects both the permeability of the cells and their organoids, and general biochemical processes in the body. Alternating magnetic field interacts with charged particles in the human body, such as ions and electrons, affecting their movement, for example, through ion channels, as well as contributing to generation of local electric fields (currents).

Thus, magnetic fields affect body tissues through the generated electric fields (currents). When affecting living systems, submolecular, molecular and supramolecular structures are involved, which results in changes at the cellular, systemic, and organismic levels.

2. Description of the Related Art

To assess the novelty of the claimed solution, a number of known technical means of similar purpose, characterized by a set of features similar to those of the claimed device are considered below.

Known is a magnetic therapy device "Almag+" https://elamed.com/dlya-domashnego-primeneniya/produksiya/almag-plus, which consists of an electronic unit, being a current oscillator, as well as four inductors in the form of applicators containing flat coils, and uses magnetic field parameters in the frequency range of 4 Hz to 16 Hz. Type and parameters of the coils used, as well as the intensity of the impact, are not disclosed.

Known is a magnetic pulse therapy device "Ortomag" http://www.gzas.ru/products/4/prod1495.html, which contains an oscillator and 6 flat coils (inductors), attachable to the human body, each of which generates pulsed magnetic field with a frequency of about 6 Hz, and an amplitude value of the magnetic field of at least 20 mT. Type and parameters of the coils used are not disclosed.

Disclosed in patent EA 201500822 is a device for local magnetic therapy, containing a current source connected to an inductor, wherein the inductor contains magnetic field concentrator, made in the form of a rod made of a magnetic conducting material, elongated in the direction of the target area. The device is characterized in that the inductor is made in the form of a set of two or more coils, located along the axis of the concentrator of coils, made by bifilar winding.

Furthermore, limited use of flat bifilar coils, called Tesla coils, is also known in magnetic therapy. Tesla coils are used in radio engineering to neutralize self-induction (inductive resistance of the coil) in order to reduce current losses. Self-induction neutralization is possible at a certain frequency of the transmitted current corresponding to the resonant frequency of "coil inductance—distributed structural capacitance" system. Resonant frequency of the system is determined by the coil design parameters—coil diameter, number of turns in windings, and wire diameter.

Known from Russian patent RU 184786 is a device for electric field therapy, containing interconnected AC source and a treatment electrode, wherein a replaceable inductor is used as the treatment electrode, in the form of a coil-capacitance, connected to a signal duration control unit, which, in turn, connected to the controller whose output is connected to the input of an AC source. The inductor is a modification of Tesla coil and is made in two forms—the coil-capacitance in the form of a flat disk and the coil-capacitance in the form of a torus. A disk coil-capacitance can be made in several modifications: a disk coil-bifilar, a disk coil-bifilar with cross-switching of turns of different wire diameters equidistant from the beginning and end of the spiral, and a disk coil-trifilar with contacts equidistant from the beginning and end of the spiral.

The device according to Russian patent RU 184786 has some design features similar to those of the claimed solution, and therefore it is accepted as a prototype.

The description of the prototype indicates that the technical result of its usage is the increase of the therapeutic intervention effectiveness at the cellular level due to the increase of the electric field impact and the depth of its penetration. However, the possibility to achieve the claimed result using this device for electric field therapy, which is, namely, the generic concept of the device according to the patent, is practically excluded, since only the combination of electric and magnetic components has penetrating effect, and it is much more difficult to stop the magnetic component than the electric one, i.e., its penetrating ability is much higher.

The disadvantage of known magnetic therapy devices is that the magnetic effect is poorly directed and is often accompanied by a significant thermal effect, expressed in the heating of nearby tissues and organs surrounding the desired area of magnetic stimulation, due to the impact of a high-intensity magnetic field on them. Targeted stimulation of local pathogenic areas in the body remains a burning issue. Moreover, many of the known devices have large dimensions and/or multiple inductors, and therefore it may be possible to use them only in healthcare facilities. The generated magnetic field is exposed to the entire volume of biological tissues in the projection of the generating electrode (inductor)—both pathological areas and tissues and obviously those not requiring external intervention, i.e., healthy. In addition, in all cases, one or more parameters of such an impact (the magnetic field intensity, field frequency, duration of impact) do not correspond to well-known and proven concepts on the safety of magnetic radiation.

BRIEF SUMMARY OF THE INVENTION

The object of the claimed invention is to provide a device for targeted local magnetic stimulating and physiotherapeutic effects that would combine the efficiency in a specific area of exposure to cells, tissues and structures of a living body, in particular, to eliminate pains of various etiologies, and at the same time would have a minimal effect on tissues and organs surrounding the area of exposure, without the occurrence of a thermal effect during their application, as well as a compact design, simplicity and ease of use, without breaking the usual routine of the user's life.

The concept of the claimed technical solution is expressed by the following set of essential features.

According to the invention, a device for magnetic effect on living bodies, containing a power source, an oscillator and an inductor connected to it, is characterized in that the oscillator operates at the resonant frequency of the inductor, which is made in the form of a flat bifilar coil with open-circuit windings, connected to the oscillator as a load in the form of a series-oscillatory circuit, providing a sinusoidal shape of the output current at the resonant frequency of the coil, wherein the bifilar coil is made in the form of a flat disk, in which the wires of its windings are placed on the dielectric substrate in the form of two concentrically arranged spirals from two adjacent wires of different windings, wherein the open-circuit terminal of one of the windings of the bifilar coil is located at the inner end of the said winding in the radial direction of the coil, and the open-circuit terminal of the second of the windings of the inductor coil is located at the outer end of the said winding in the radial direction of the coil, and the opposite terminals of both coil windings are connected to the corresponding terminals of the oscillator.

This set of essential features of the claimed invention is sufficient to solve the technical problem, specified by the applicant, and to achieve the technical result provided by the invention.

In addition, the claimed technical solution is characterized by a number of additional optional features:

the inductor can be structurally combined with the oscillator;

the windings of the bifilar coil can be made as two identical wires put together, located in the winding plane with a tight junction of all the wires to each other providing total thickness of the winding equal to one wire diameter;

the windings of the bifilar coil can be made as two identical wires put together with winding wires located perpendicular to the coil plane providing total thickness of the winding equal to two wire diameters;

the oscillator can be made in the form of a self-excited oscillator of sinusoidal or square oscillations with a coil in the circuit of the positive current feedback (PCF);

the oscillator can be made in the form of a self-excited oscillator of sinusoidal oscillations with a coil in the PCF circuit with amplitude modulation or manipulation;

the oscillator can be equipped with the circuit of the negative voltage feedback (NVF) with the ability to control the magnitude of the output voltage and, accordingly, the output current and intensity of the magnetic field generated by the inductor by changing the depth of the NVF;

the oscillator can be made in the form of a voltage-controlled oscillator with the phase-locked loop (PLL);

the resonant frequency of the bifilar coil, as a series-oscillatory circuit, and the frequency of the oscillator is set in the range of 250-380 kHz.

The claimed set of essential and optional features ensures the achievement of a technical result, which resides in the fact that the device for magnetic effect ensures the formation of a directed magnetic effect on human tissues and organs by the inductor with the formation of an inhomogeneous magnetic field of essentially conical shape providing maximum intensity of such an effect, i.e., the maximum intensity of the magnetic field located at the top of the said cone. The implementation of the device in a compact, ergonomic form increases the level of positive emotions of users during its use, promotes the patients' adherence to treatment, i.e., to compliance, which results to higher rates of treatment success.

BRIEF DESCRIPTION OF THE DRAWINGS

The invention is illustrated by the drawings, where.

Figure 1:
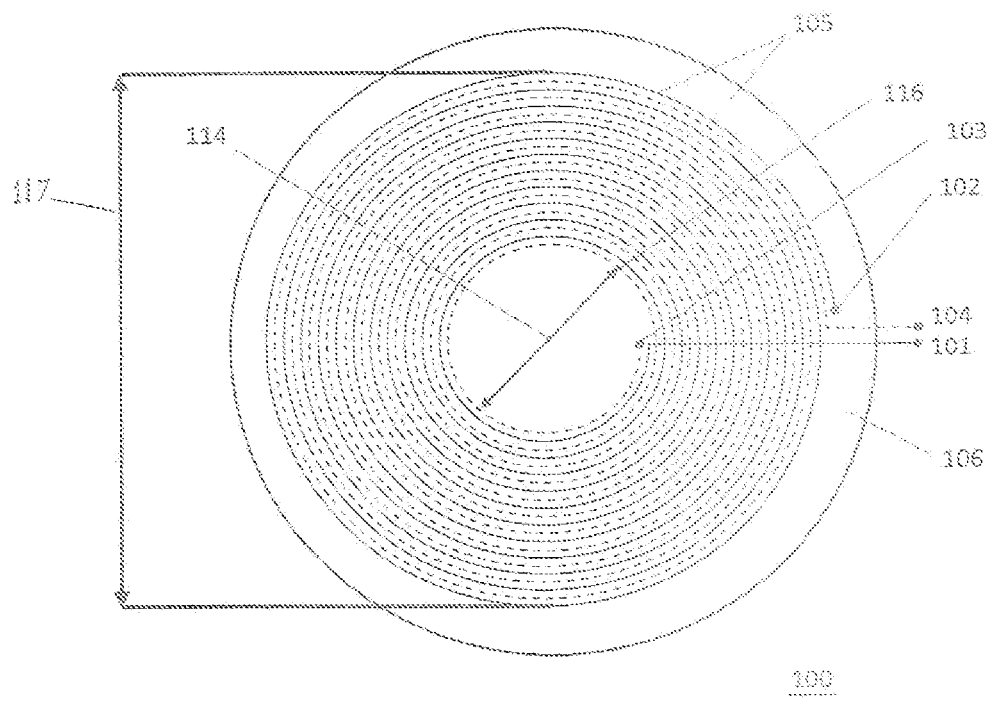
FIG. 1 shows a structural view of an inductor made in the form of a flat bifilar coil.
Figure 2:
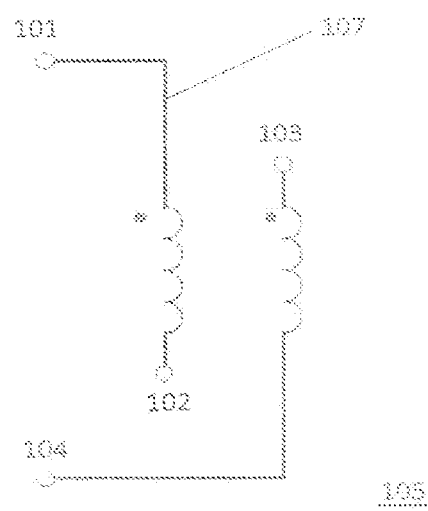
FIG. 2 shows an electrical diagram of the windings of a flat bifilar coil.

In the drawings, positions and letters designate the following: 1—the claimed device, 100—the inductor; 101, 201—the first (closed-circuit) terminal of the first winding; 102, 202—the second (open-circuit) terminal of the first winding; 103, 203—the third (open-circuit) terminal of the second winding; 104, 204—the fourth (closed-circuit) terminal of the second winding; 105, 205—L1—the bifilar coil of the inductor; 106—a substrate; 107—the first winding of the bifilar coil; 108—the second winding of the bifilar coil; 109—the oscillator; 110—the power source; 111—the inductor housing; 112—the oscillator housing; 113—connecting cable for connecting the inductor to the oscillator;

114—axis of the bifilar coil; 115—the oscillator unit; 116—inner diameter of the bifilar coil; 117—outer diameter of the bifilar coil; 118, 119—the oscillator outputs; 120—oscillator in the form of an oscillator with the PLL; 200—oscillator in the form of a self-excited oscillator with a bifilar coil in the PCF circuit; 121, 221—amplifying stage covered by feedback loops; 122, 123, 124, 222, 223, 224—resistors; 125, 126, 225, 226—inputs of the amplifying stage; 127, 227—outputs of the amplifying stage; 128—phase-lock loop (PLL) node; 129—low-pass filter (LPF); 130—PLL output voltage waveform switch; 130.1, 130.2—positions of the switch 130; 131—phase detector (PD); 132—voltage-controlled oscillator (VCO); 133, 233—test point of the output voltage of the oscillator with the PLL and test point of the output voltage of the self-excited oscillator, respectively; 134, 234—test point of the output current of the coil; 135—test point of the output voltage of the PLL node, U1—output voltage at the test point 233 of the self-excited oscillator 200; U2—voltage, corresponding to the output current, at the test point 234 of the self-excited oscillator 200; U3—output voltage at the test point 133 of the oscillator 120 with the PLL in the position 130.1 of the switch 130; U4—voltage at the test point 135 of the PLL node in the position 130.1 of the switch 130; U5—voltage at the test point 134 of the oscillator 120 with the PLL, corresponding to the output current in the position 130.1 of the switch 130; U6—output voltage at the test point 133 of the oscillator 120 with the PLL in the position 130.2 of the switch 130; U7—voltage at the test point 135 of the PLL node in the position 130.2 of the switch 130; U8—voltage at the test point 134 of the oscillator 120 with the PLL, corresponding to the output current in the position 130.2 of the switch 130.

DETAILED DESCRIPTION OF THE INVENTION

Figure 12:
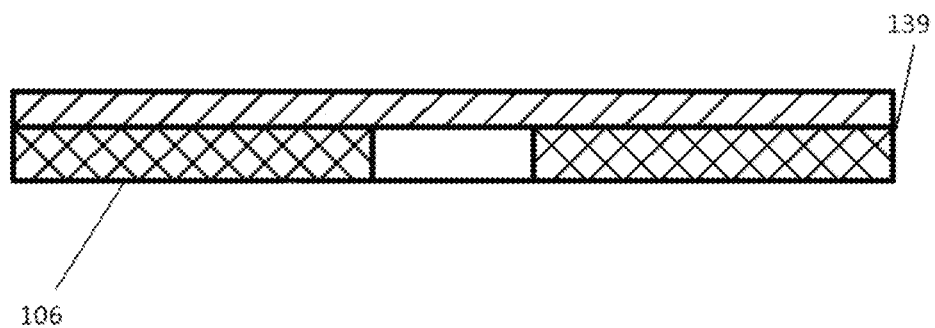
FIG. 12 shows the cross-section of the coil according to one of its embodiments.

The flat bifilar coil 105, 205 of the inductor is formed by two identical conductors, also called winding wires, wound in two wires in one layer in one (horizontal) plane, in the form of a flat spiral from the inner diameter 116 to the outer diameter 117, with a snug fit of adjacent conductors and adjacent turns of windings to each other without gaps between them. This arrangement of windings is shown in FIG. 12, where 139 is a cross-section of the coil 105 (205) with two wires, put together in a horizontal plane and placed on the substrate 106. Adjacent conductors form, respectively, the first winding 107 and the second winding 108 of the flat bifilar coil 105, 205. The windings 107, 108 can be wound with a single-core or multi-core winding wire in enamel or varnish insulation. The thickness of the bifilar coil 105, 205 is equal, respectively, to the thickness of one winding wire.

Figure 13:
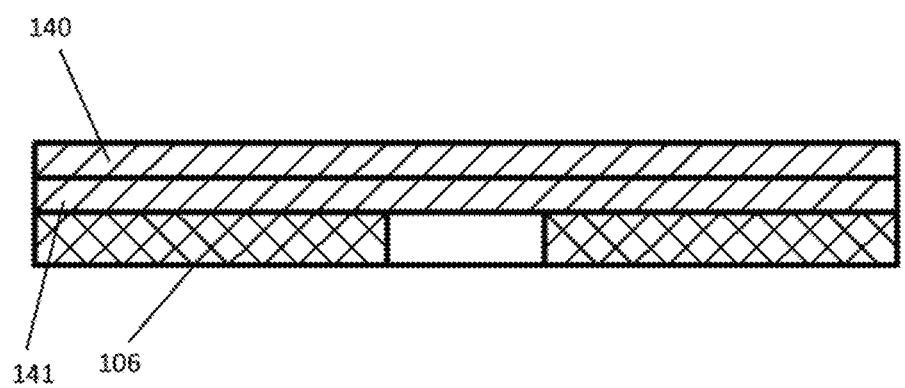
FIG. 13 shows the cross-section of the coil according to its another embodiment.

The windings 107, 108 of the bifilar coil 105, 205 can be made by spiral winding in one plane into two identical wires put together with a vertical arrangement of winding wires, i.e. perpendicular to the plane of its winding, with "two wires—to two wires" adjoining each other, while providing the total thickness of the winding equal to two diameters of the winding wire. This arrangement of windings is shown in FIG. 13, with the cross-sectional view of the following: 140—one of the wires of the coil 105 (205), placed on the other wire 141, and both wires are put together in a vertical plane and placed on the substrate 106.

The bifilar coil 105, 205 can also be made in the form of two flat windings with a thickness of one wire, located with their planes opposite and parallel to each other on different sides of the substrate 106, i.e. with the separation of both windings of the coil by the substrate 106 (this option is not shown).

The first winding 107 of the coil 105, 205 has a first terminal 101, 201 and a second terminal 102, 202. The second winding 108 of the coil 105, 205 has a third terminal 103, 203 and a fourth terminal 104, 204, respectively. The second and the third terminals 102, 103, 202, 203 of the coil 105, 205 are open-circuit ones. The open (open-circuit) terminal 102, 202 of the first winding 107 of the coil 105, 205 is located at the inner end of the said winding in the radial direction of the coil, and the open (open-circuit) terminal 103, 203 of the second winding 108 of the coil 105, 205 is located at the outer end of the said winding in the radial direction of the coil.

It is possible to have a reverse arrangement of open-circuit terminals of the coil 105, 205, wherein the open (open-circuit) terminal 102, 202 of the first winding 107 of the coil 105, 205 is located at the outer end of the said winding in the radial direction of the coil, and the open (open-circuit) terminal 103, 203 of the second winding 108 of the coil 105, 205 is located at the inner end of the said winding in the radial direction of the coil.

The first (closed-circuit) terminal 101, 201 of the first winding 107, located at the outer end of the said winding in the radial direction of the coil 105, 205, and the fourth (closed-circuit) terminal 104, 204 of the second winding 108, located at the inner end of the said winding in the radial direction of the coil 105, 205, are generally connected to signal source or self-excited oscillator circuit with a two-wire cable.

The windings 107, 108 of the bifilar coil 105, 205 are placed on the flat substrate 106 in the form of a round plate made of a dielectric material, such as, for example, plastic or wood. In this case, as shown in FIG. 1, terminal 101 of the first winding 107 and terminal 104 of the second winding 108 are brought out outside the substrate 106 to connect them to the outputs 118 (133, 233), 119 (134, 234) of the oscillator 109 (120, 200), and the opposite open-circuit terminals 102 and 103 of the said windings are sealed in the substrate 106 and not brought out outside the coil.

In electrical equivalent, the coil 105, 205 is a series-oscillatory circuit, in which inductance is formed by the wires of the windings, and the capacitance is formed structurally, between the wires of the windings, and is distributed along the entire length of the windings.

Figure 3:
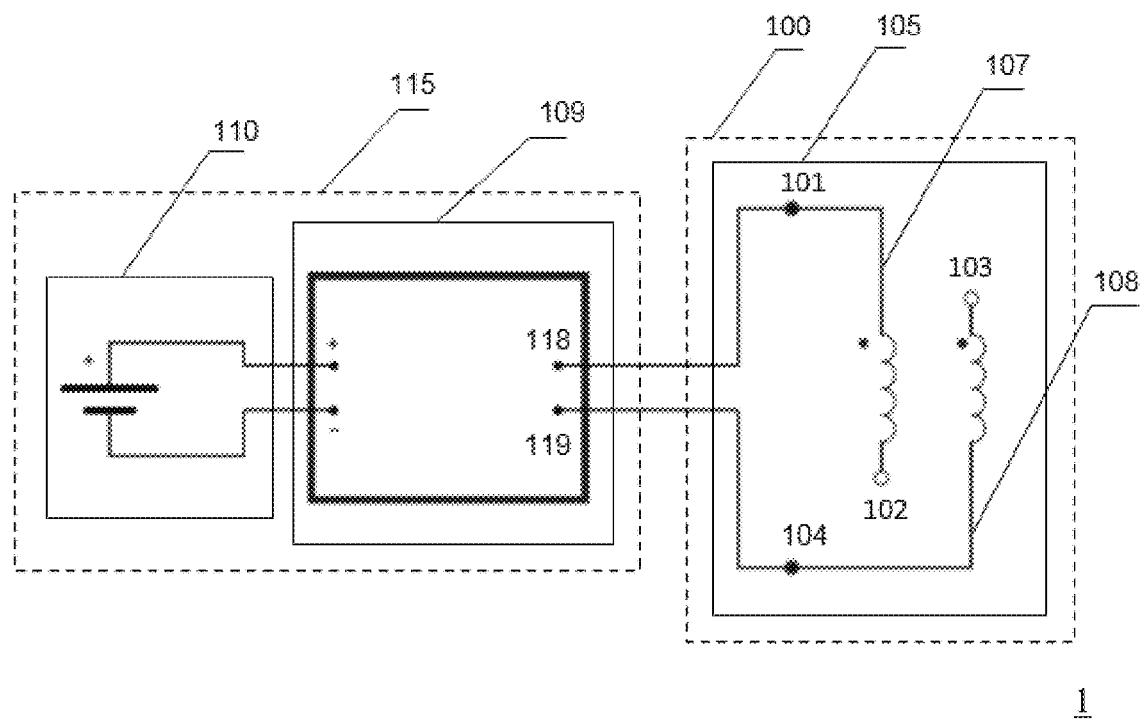
FIG. 3 shows the claimed device in the form of a connection diagram of a power source, an oscillator and an inductor.
Figure 4:
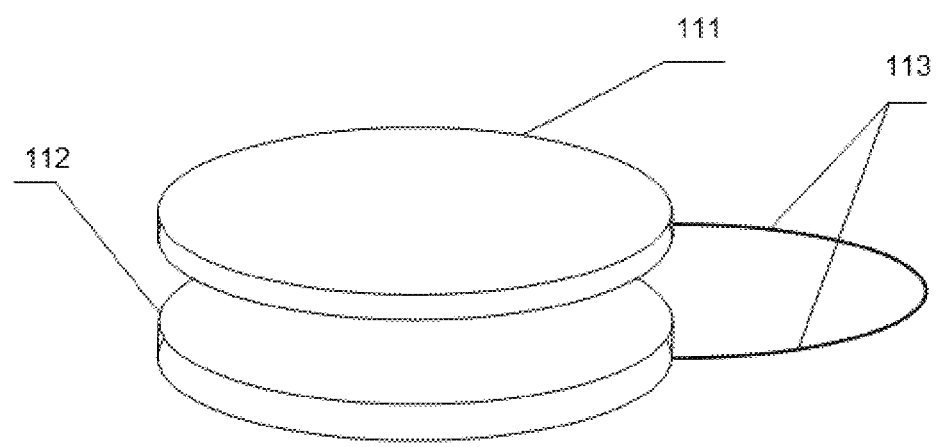
FIG. 4 shows a general view of the oscillator and the inductor made, respectively, in the form of a round device and a flat disk.
Figure 5:
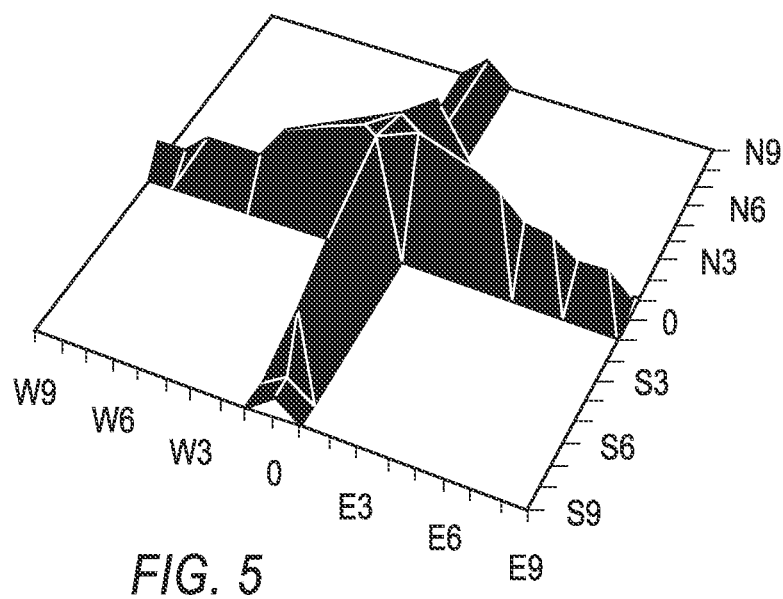
FIG. 5 shows a graph, representing the shape of the intensity of the generated magnetic field.
Figure 6:
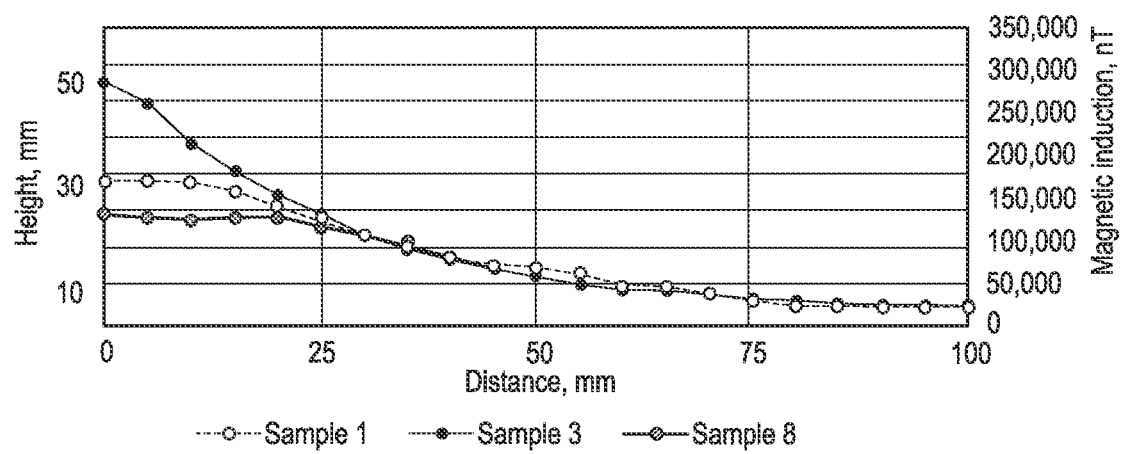
FIG. 6 shows a graph of the bifilar coil magnetic field intensity distribution along its vertical and horizontal axes.

In the embodiment, shown in FIGS. 3, 4, the coil is structurally isolated from the oscillator, the first terminal 101, 201 and the fourth terminal 104, 204 of the coil 105, 205 are connected to the voltage outputs 118 and 119 of the oscillator 109. The oscillator 109 is connected to a DC power source 110, which can be a rechargeable battery.

Depending on the embodiment of the device for magnetic effect, the oscillator and the coil can be combined in a common housing. The oscillator can be powered from the AC mains through an AC or DC adapter.

On the housing of the inductor (or on the housing of the device containing the inductor), fastening means can be provided for the attachment to the user's clothing in the area of the desired magnetic stimulating or physiotherapeutic effect to eliminate the need to hold the device during operation.

The oscillator 109 schematically can be an oscillator with manual tuning to a resonant frequency or a self-excited oscillator 200 with the PCF circuit, or a voltage-controlled oscillator 120 with the PLL, and the inductor 100 is a series-oscillatory circuit, which is the load of the said oscillator, inducing a magnetic field.

Figure 7:
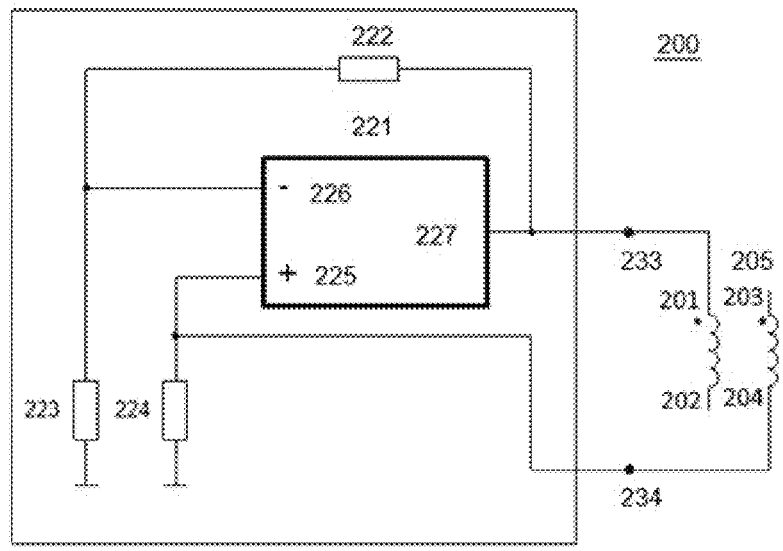
FIG. 7 shows a functional diagram of an embodiment of the oscillator, particularly, in the form of a self-excited oscillator with a bifilar coil in the PCF circuit.

The functional diagram of an embodiment of the oscillator 200 with a coil 205 in the circuit of the positive current feedback is shown in FIG. 7. The amplifying stage 221 of the self-excited oscillator is covered by feedback loops, formed by resistors 222, 223, 224 and the coil 205. Resistors 222 and 223 are elements of the negative voltage feedback (NVF), wherein the voltage from the output 227 is fed through a resistive voltage divider, formed by resistors 222 and 223, to the inverse ("−") input 226 of the stage 221. These resistors 222 and 223 determine the transmission coefficient of the self-excited oscillator (the voltage value at its output 227). Resistor 224 is a current sensor in the circuit of the positive current feedback (PCF), wherein the output voltage of the amplifying stage 221, through the voltage divider, formed by the resistor 224 and the coil 205, is fed to the direct ("+") input 225 of the stage 221. In this case, the voltage on resistor 224, which is a current sensor, is proportional to the output current, 233 is the output voltage test point and 234 is the output current test point.

Figure 9:
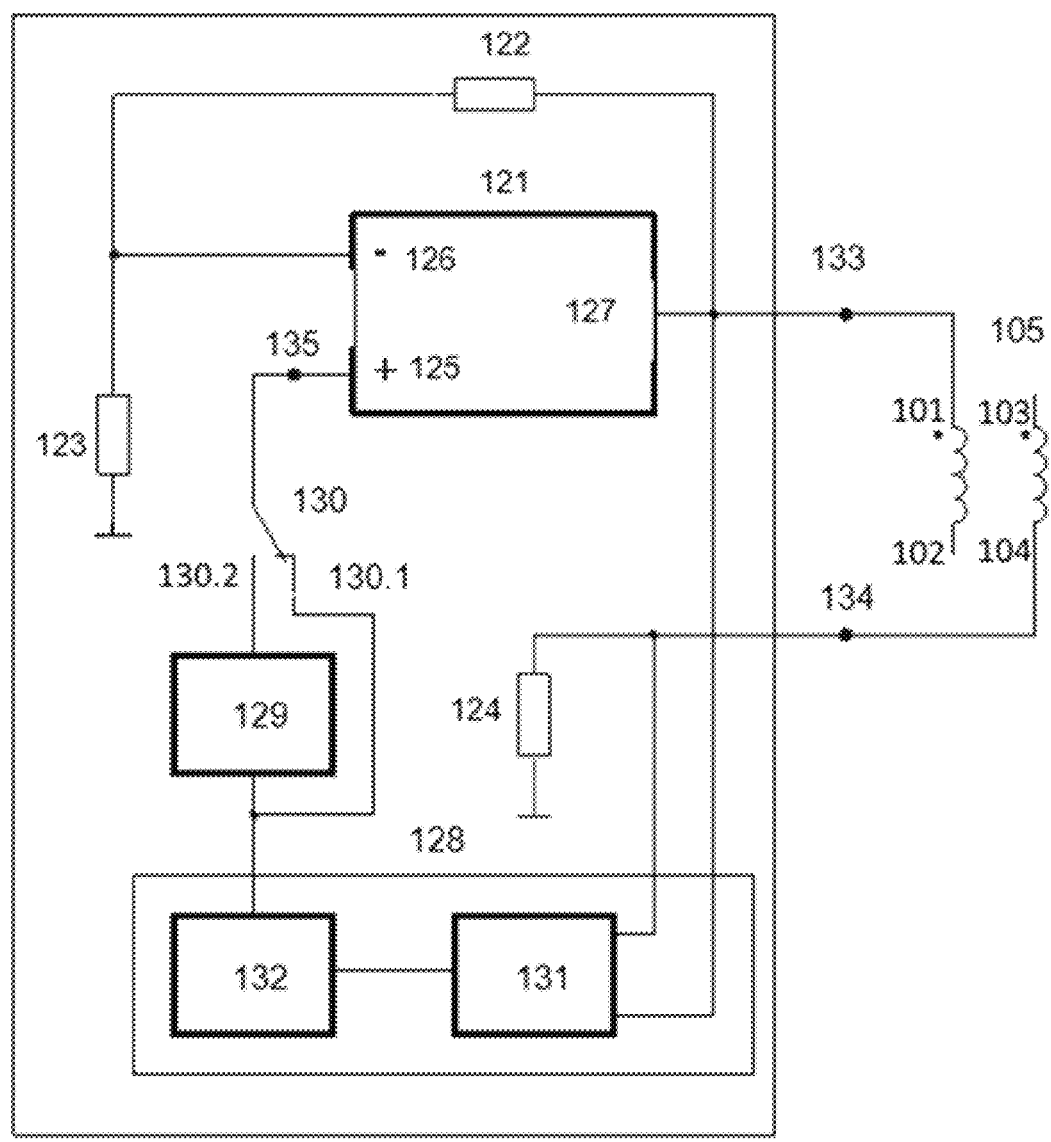
FIG. 9 shows a functional diagram of another embodiment of the oscillator, particularly, in the form of an oscillator with the PLL.

The functional diagram of an embodiment of the oscillator in the form of an oscillator 120 with the PLL is shown in FIG. 9. It contains a coil 105; amplifying stage 121; the PLL node 128 containing a phase detector (PD) 131 and a voltage-controlled oscillator (VCO) 132; a low-pass filter (LPF) 129; an output voltage waveform switch 130 of the PLL node 128 (sinusoidal or in the form of square-wave pulses). The amplifying stage 121 is covered by feedback loops, formed by resistors 122, 123, 124 and the coil 105. Resistors 122 and 123 are elements of the NVF, wherein the voltage from the output 127 of the stage 121 (which is also the output of the self-excited oscillator 120) is fed through a resistive voltage divider, formed by resistors 122 and 123 to the inverse ("−") input 126 of the amplifying stage 121. The resistors 122 and 123 determine the transmission coefficient of the self-excited oscillator (the voltage value at its output 127). Resistor 124 is a current sensor in the PCF circuit, wherein the output voltage of the amplifying stage 121, through the voltage divider, formed by the resistor 124 and the coil 105, is fed to the PLL node 128 and then, depending on the position of the switch 130, either directly or through the LPF 129—to the direct ("+") input 125 of the stage 121. In this case, the voltage on the resistor 124, which is the current sensor, is proportional to the output current, 133 is the output voltage test point, 134 is the output current test point, and 135 is the PLL node 128 output voltage test point.

The amplifying stage 121, 221 can be a powerful operational amplifier in an integrated form, covered by feedback loops, or a transistor multi-stage voltage amplifier made according to the circuitry of operational amplifiers: an input stage, a voltage amplification stage, an output repeater.

In the author's version, the amplifying stage was made on BC856B, BC846B, BCP53 (BD677), BCP56 (BD678) transistors.

The PD 131 usually contains appropriate logic or transistor comparators for current and voltage signals, converting a sinusoidal waveform to a square one. In this case, resistive dividers are installed at the inputs of the comparators to equalize the slope of the voltage and current signals at the inputs of the comparators in order to maintain the accuracy of the PD operation. The phase comparison element in the PD can be a logical element "Exclusive OR" ("XOR").

The PD 131 can also be made on the basis of a specialized microchip.

The signal at the output of the PD 131 is proportional to the phase difference of the voltage and current signals.

In one of the author's versions, the PD 131 was made on the basis of microchips: MAX942CSA—comparators; SN74AHC1G86DBV—a phase comparison element.

VCO 132 can be implemented:
in the integrated form on logic elements;
in the transistor form;
on the basis of a specialized microchip.

LPF 129 is needed to allocate the sinusoidal waveform of the signal when the VCO is operating in the square oscillation mode.

LPF 129 is a multi-stage filter based on operational amplifiers or transistors. The filter transmission coefficient approximation characteristic and filter order are selected based on obtaining the minimum distortion of the output sine-wave signal and the maximum suppression of inherent harmonics.

In the author's version, the LPF 129 was a 3-stage Chebyshev filter of the 2nd order on the AD812 microchips.

The entire AFC node 128, with the exception of comparators, can be made on the basis of a specialized microchip.

In the author's version, the PLL node 128 was made on the CD4046BE microchip, including a PD and a VCO.

The claimed device 1 operates as follows.

The oscillator 109 generally supplies voltage to the coil 105, 205 at the resonant frequency of the coil.

Tuning to a known resonant frequency of the coil can be done manually by the controls of the oscillator 109.

Tuning to the resonant frequency can be done automatically in the circuit of the self-excited oscillator 200 with the PCF.

Tuning to the resonant frequency of the coil can be done automatically in the circuit of the oscillator 120 with the PLL.

In the self-excited oscillator 200 (FIG. 7), the process of excitation of self-oscillations is carried out as follows. When the self-excited oscillator is powered through the resistor 224, the PCF circuit is closed and maintained. In this case, the classical conditions for the occurrence and maintenance of self-oscillations due to the PCF circuit—phase balance and amplitude balance—are met. Self-oscillations occur at the resonant frequency of the coil 205, since it is for this frequency that the maximum current occurs on this bifilar coil, which is a series-oscillatory circuit.

Figure 8:
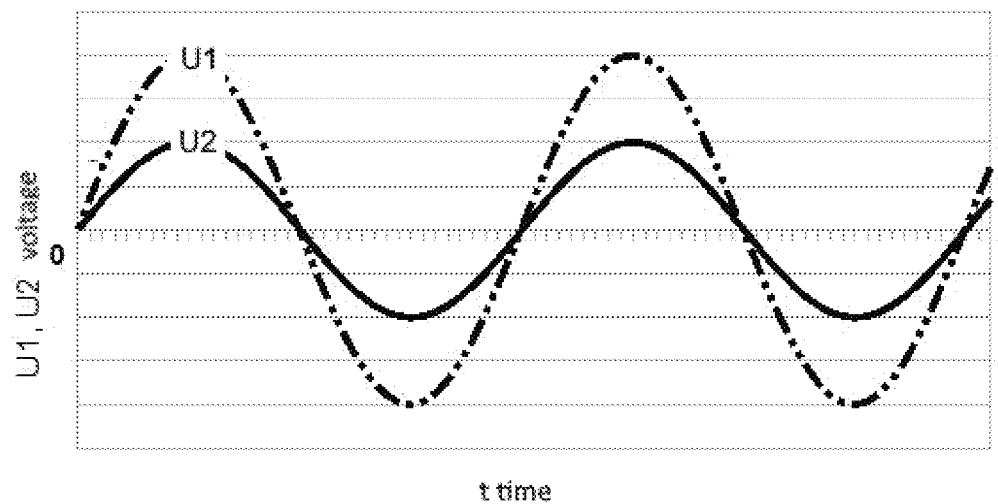
FIG. 8 shows voltage distribution diagrams at test points of the self-excited oscillator with the PCF circuit.

The output voltage U1 (FIG. 8) and the output current, shown as U2, have sinusoidal waveform and coincide in phase. The output voltage value is stabilized using a chain of resistors 222 and 223 of the NVF circuit. The voltage distribution diagrams at test points 233 and 234 are shown in FIG. 8. The designation U1, shown by the dash-dotted line, is the voltage waveform at test point 233, and the designation U2, shown by the normal line, is the voltage waveform at test point 234. When the resistance value of the resistor 224 is 1 Ohm, it coincides with the current waveform with an accuracy of instantaneous values.

The process of generating oscillations on a resonant coil in the oscillator in the form of an oscillator 120 with the PLL (FIG. 9) is as follows. When power is fed to the self-excited oscillator 120, the VCO 132 of the square-wave signal in the PLL node 128 is switched on. The frequency of this signal is in the range of expected values of the resonant frequencies of the connected coils, i.e. 250 . . . 380 kHz (this range is programmed by the internal switching circuit of the PLL node 128, for example, by selecting the appropriate frequency-setting elements—a resistor or a capacitor (this circuit is not shown)).

If the switch 130 is in position 130.1, the square-wave signal, through the amplifying stage 121, goes to the output of the self-excited oscillator 120, i.e. to the input of the coil 105. Due to the fact that the coil 105 is a series-oscillatory circuit, shock excitation of this circuit by a square-wave voltage signal results to the occurrence of sinusoidal current oscillations (called in classical theory forced oscillations from external excitation). These oscillations occur at the resonant frequency of the coil 105, since it is for this frequency that the maximum current occurs on the coil—a series-oscillatory circuit. Since at the initial moment of generation, the frequency value of the output voltage of the PLL node 128 may not coincide with the value of the resonant frequency of the coil 105, there is a mismatch of the voltage and current phases on the coil. The signals, corresponding to the voltage and current phases, are received at the input of the phase detector (PD) 131 of the PLL node 128, where the phases are compared and the error signal is generated. The voltage of the error signal of the PD 131 controls the frequency of the VCO 132, bringing it closer to the resonant frequency of the coil 105 and providing a zero phase shift of the voltage and current phases on the coil.

If the switch 130 is in position 130.2, the square-wave signal of the PLL node 128 first enters the low-pass filter (LPF) 129, where the first harmonic of the fundamental frequency of the sine-wave signal, corresponding to the square-wave frequency, is extracted from it. Then, this sine-wave signal, through the amplifying stage 121, goes to the output 127 of the self-exited oscillator, i.e., to the input of the coil 105, and the frequency is auto-tuned by the PLL node 128 to a zero phase shift in the same manner as described above.

Figure 10:
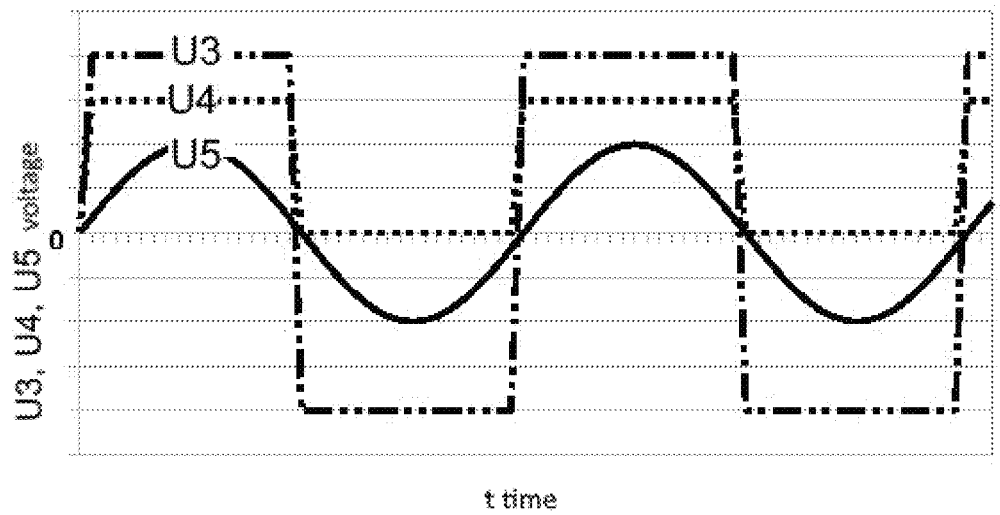
FIGS. 10 and 11 show the voltage distribution diagrams at test points of the oscillator according to FIG. 9.

The voltage distribution diagrams at test points 133, 134, and 135 in position 130.1 of the switch 130 are shown in FIG. 10. The designation U3, shown by the dash-dotted line, is the voltage waveform at test point 133. The designation U4, shown by the dotted line, is the voltage waveform at test point 135. The designation U5, shown by the solid line, is the voltage waveform at test point 134. When the resistance of the resistor 224 is 1 Ohm, the voltage waveform at test point 134 coincides with the current waveform with an accuracy of instantaneous values.

Figure 11:
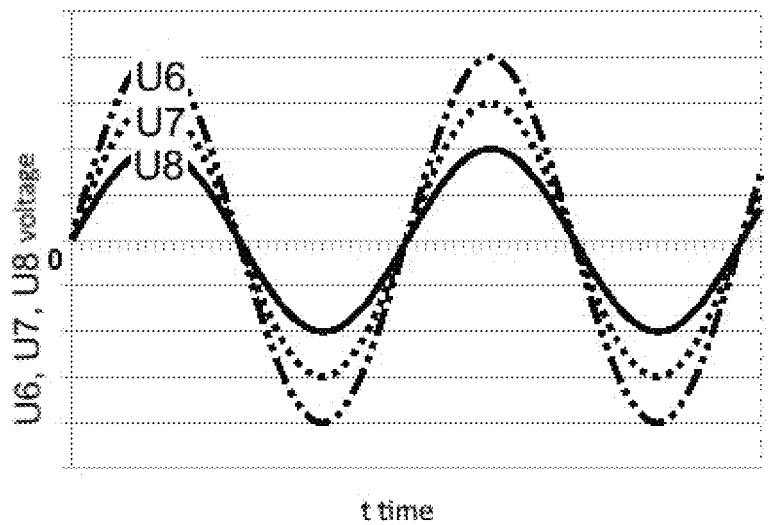

The voltage distribution diagrams at test points 133, 134 and 135 in position 130.2 of the switch 130 are shown in FIG. 11. The designation U6, shown by the dash-dotted line, is the voltage waveform at test point 133. The designation U7, shown by the dotted line, is the voltage waveform at test point 135. The designation U8, shown by the solid line, is the voltage waveform at test point 134. When the resistance of the resistor 224 is 1 Ohm, the voltage waveform at test point 134 coincides with the current waveform with an accuracy of instantaneous values.

The need to be able to excite the coil 105 with two voltage signals, square-wave or sine-wave signal, is associated with different effects for various diseases. Thus, the square-wave voltage enriches the output current (field) waveform with higher harmonics, providing a more aggressive effect.

The implementation of the oscillator in the form of a self-excited oscillator simplifies the implementation of the claimed device and provides automatic excitation of oscillations in the inductor coil at its resonant frequency.

During the process of induction, due to the multiplication of magnetic field intensity in the coil, a conical shape of the magnetic field is achieved with a maximum intensity at the top of the cone due to a decrease in the density of turns from the center to the edge of the coil 105, 205. In this case, the height of the cone above the surface of the coil 105, 205 depends on the diameter of the coil and the strength of the induction current through the coil.

The inner diameter 116 of the bifilar coil 105, 205 essentially determines the diameter of the toroid, formed at the top of the cone of the magnetic field inductor, generated by the coil 105, 205 due to the interference of individual magnetic fields, generated by each of the turns of the windings of the bifilar coil 105, 205.

Table 1 presents the values of the magnetic field intensity (in $\mu T$), measured along the mutually perpendicular directions N, W, E, S in the plane of the coil 105.

TABLE 1

| Displacement from the center, cm | N | S | W | E |
|---|---|---|---|---|
| 0 | 4 | 4 | 4 | 4 |
| 1 | 4 | 4 | 4 | 3.6 |
| 1.5 | 3.8 | 3.6 | 3.8 | 3 |
| 2 | 3 | 3 | 3.4 | 1 |
| 3 | 2 | 2 | 2 | 1 |
| 4 | 1 | 1 | 1 | 1 |

Table 2 presents the values of the magnetic field intensity (in $\mu T$), measured along the mutually perpendicular directions N, W, E, S at a distance of 5 cm from the plane of the coil.

TABLE 2

| Displacement from the center, cm | N | S | W | E |
|---|---|---|---|---|
| 0 | 5.4 | 5.4 | 5.4 | 5.4 |
| 1 | 5 | 5.6 | 5 | 5.4 |
| 2 | 4.6 | 5.4 | 4.6 | 5 |
| 3 | 4 | 5.2 | 4 | 4.6 |
| 4 | 3.4 | 4.8 | 3.4 | 4 |
| 5 | 1 | 4.2 | 2 | 3 |
| 6 | 1 | 3.6 | 2 | 2.8 |
| 7 | 1 | 3 | 2 | 2 |
| 8 | 1 | 1 | 1 | 2 |
| 9 | 1 | 1 | 1 | 1 |

The shape of the distribution of the magnitude of the magnetic field intensity of the coil 105, 205 has the characteristic shape of a truncated cone and in projection onto the plane of the base reflects the features of its winding.

The resonant frequency of the series-oscillatory circuit implemented in the claimed device in the form of a bifilar coil 105, 205 is determined by the parameters of the coil 105, 205, in particular its geometrical dimensions, the number of turns of its windings, the inner and outer diameter of the windings, as well as the diameter (cross-section) and length of the winding wire. The length of the wire with the selected cross-section is determined by the dimensions of the coil, the method of winding and the number of turns.

Coils of different sizes can cause a comparable physiotherapeutic effect, and the most significant in terms of achieving a stimulating and physiotherapeutic effect is the directional shape of the resulting magnetic field, as well as its frequency and magnitude of intensity. In this case, most of the above parameters are determined by the geometric parameters of the coil 105, 205 of the inductor 100. The excitation of oscillations, and, accordingly, the generation of a magnetic field by an inductor, occurs at the resonant frequency of the coil 105, 205 of the inductor 100. The oscillations of the coil current are always sinusoidal. In order to stabilize oscillations and reduce non-linear distortions, the circuit can additionally be covered by the NVF circuit.

Thus, the oscillatory circuit, made in the form of a bifilar coil with open loops, acts both as a frequency-setting element and at the same time as a load of an oscillator—a magnetic field inductor.

The resonant frequency of the oscillatory circuit, formed by the inductor coil, is 250-380 kHz, preferably 280-350 kHz. The said frequency range is a frequency range, determined on the basis of studies as the most effective and safe operating frequency range of the generated magnetic exposure in terms of providing the best and stable stimulating and therapeutic effect.

Due to the influence of an alternating magnetic field, the most pronounced and stable magnetic stimulating and physiotherapeutic effect is provided in the above range of resonant frequencies of the oscillatory circuit, which consists in eliminating pain syndromes, stimulating vital processes and regeneration, accelerating the restoration of human and animal tissues after invasive influences and injuries.

The oscillator is configured to control the magnitude of the output voltage and, accordingly, the magnitude of the output current and intensity of the magnetic field, generated by the inductor. The oscillator can also be provided with means for controlling the duration, number of cycles or periodicity of repetition of the generated magnetic effect, as well as its modulation and manipulation of low-frequency signals.

The intensity of the impact can be pre-set by the parameters of the oscillator and set in the most effective and safe for the user range of 80 µT to 200 µT, and, in this case, it may be possible to control only the duration of exposure. The experiments showed that the magnetic effect generated by the inductor according to the present invention, with a magnetic field intensity in the range of 80 µT to 200 µT, provides a stable physiotherapeutic effect, while the magnetic field intensity on the inductor surface remains comparable to the magnitude of the Earth's magnetic background, being of about 50-60 µT, which provides a minimal effect on human tissues and organs surrounding the area of exposure, and thereby also eliminates the occurrence of an undesirable thermal effect.

The shape of the magnetic field provided by the claimed device allows a directed magnetic stimulating effect on human tissues and organs located directly below the place of application of the inductor at a depth of up to 6 cm from the surface of the body. Exposure to such a magnetic field by applying the said inductor to parts of the body, located above pathogenic areas, in particular above the painful organs for 15-30 minutes, provides a directed local effect on the exposed parts of the body with relief of pain for a long period of time. In this case, the shape of the magnetic field of the claimed device allows virtually eliminating the main side effect in the form of exposure to a magnetic field when applying devices known from the prior art to healthy tissues surrounding the area of the desired effect, in particular magnetic stimulation, which can sometimes cause the development of new pathologies or amplification of old ones. This disadvantage is eliminated due to the use of a "focused" magnetic field with a maximum of its intensity, concentrated at the top of the "magnetic cone", i.e. limited to a small area of "directed" exposure.

A series of experiments with the claimed device showed that the therapeutic effect of eliminating or reducing pain syndromes of various etiologies is achieved primarily due to the properties of the applied inhomogeneous and directed magnetic field. The range of resonant frequencies of 250-380 kHz, determined by the results of the experiments, as well as the magnetic field intensity range of 80-200 µT, make it possible to obtain an even more pronounced magnetic stimulating and physiotherapeutic, in particular analgesic effect, without the danger of local heating of nearby tissues.

Example 1. TESTING ON THE PROLIFERATION MODEL

The study was conducted at the "Scientific Center for Cytogenetic Testing", LLC in January 2019.

The device was tested at different device capacities, namely, at 50% (90-100 µT) and 100% (180-200 µT), and at different distances (0 cm and 4 cm) in order to determine the effect of the device on the proliferation of cells of the CHO-K1 line.

Cells were plated at 200 µl of medium per well of a 96-well plate. The medium was 9 parts of DMEM (or DMEM Needle) culture medium supplemented with 1 part of fetal calf serum. A suspension of cells was prepared at a seed concentration of $2\times10^4$ cells/ml. For this, culture vials (25 cm$^2$ or 75 cm$^2$ in area) with a formed monolayer of cells (2-4-day cell culture with normal cell morphology) were selected; cell monolayer was dispersed: 2-5 ml of growth medium was added to the culture vial; the contents of the vial was mixed with a 10 ml pipette; a sample was taken and the cell suspension was transferred to an Eppendorf type microcentrifuge tube. Then, the cell concentration in the Gorjaev's chamber was calculated. The cell suspension was diluted with growth medium to the desired final cell concentration. 0.2 ml of cell suspension was added to the required number of wells (based on the number of test samples) in two 96-well plates. Cell plates were incubated for three days at 37±0.5° C. in an atmosphere with 5±0.7% $CO_2$ on different shelves of the incubator. Moreover, the control plate was placed on the shelf, and the experimental ones were placed strictly in the middle directly on the switched-on device for magnetic effect and at a distance of 4 cm from the surface, using plastic bathtubs or tripods as a height elevator. This scheme was repeated with the power of the switched-on device 50% and 100%. At the end of the incubation period, the plates were removed from the incubator, the entire growth medium was removed from the wells, 100 µl of trypsin-versene solution (1:9) was poured and left for 10-15 minutes till complete detachment of cells from the substrate. The contents of the well was mixed with a dispenser and 10 µl was added to the Gorjaev's chamber. Cell counting was performed cornerwise in five large squares. The resulting number was multiplied by a factor of 1.25 and 104, and thus the number of cells in ml was determined. The procedure was repeated for each well. Then, the proliferation index (PI) was calculated as the ratio of cell concentration after three days of cultivation to the seed concentration. PIs for control and the experiment are calculated separately. Then, the Impact Index was calculated as the ratio of the experimental and control options according to the formula: ((test IP/control IP)*100−100).

The test results showed that proliferation increases by 7-40% depending on the intensity of exposure and the distance from the plate to the device.

Example 2. TESTING ON THE "WOUNDS" MODEL

Testing to determine the specific activity of the device on a wound model ("wound healing assay"). The in vitro wound model is a widely used technique for assessing cell mobility and migration rate. During the healing of an experimental wound, different types of cells react in a similar way: the cells polarize, form protrusions towards the wound and migrate. The study was conducted at the "Scientific Center for Cytogenetic Testing", LLC in compliance with the standard protocol for this procedure.

The study showed an increase by 12% in the "wound" healing rate in cell culture when using the device according to the invention.

Example 3. TREATMENT OF HEMORRHOIDS

In February 2019, in St. Petersburg, on the basis of private health care facilities, the device was tested on men with symptoms of hemorrhoids of 3-4 degrees (20 people aged 30 to 60 years). The tests were aimed at studying the effect of relieving pain and other senses of discomfort. Magnetic therapy sessions were carried out for 14 days for 30 minutes each day at a magnetic field intensity of 180-200 µT (100% of the device's power). Such a magnetic field excludes the occurrence of undesirable side effects, in particular, the thermal effect. The patient applied the magnetic disk to the area of maximum pain. The selected group included both patients taking additional medications and patients not receiving medical treatment. All patients who participated in the study described the disappearance of characteristic pain on the day 2-3 after the beginning of the study; in some cases there was a cessation of bleeding in acute forms of the disease and a decrease in tumor and edema after 14 days upon the end of the therapy. In each case, the proctologist performed an objective examination before and after magnetic therapy sessions, which confirmed the subjective feeling of remission.

Example 4. TREATMENT OF PROSTATITIS

In February 2019, in St. Petersburg, on the basis of private health care facilities, the device was tested on men with symptoms of prostatitis. The study involved 20 men aged 40 to 60 years. The patient applied the magnetic disk to the area of maximum pain. The selected group included both patients taking additional medications and patients not receiving medical treatment. As a result, a positive effect of the subjective feeling of pain reduction over 10-14 days was observed according to the described method. Objective confirmation of the test results is based on laboratory analysis of the number of lymphocytes in a special secret, which showed a decrease in the number of lymphocytes by 12-15% as a result of using a magnetic device. It is assumed that a significant increase in the efficiency of the impact when implementing direct access to the disease focus is possible by changing the design parameters of the device, resulting in an increase in the intensity of the acting magnetic field in the pathogenic area.

Example 5. MENSTRUAL PAIN SYNDROME

The study was also conducted on the basis of private health care facilities in February 2019. The study voluntarily involved 50 women aged 18 to 24 years with menstrual pain syndrome. Magnetic therapy sessions were carried out for 2-4 days for 30 minutes each day at a magnetic field intensity of 180-200 µT (100% of the device's power). The study revealed positive dynamics based on subjective feelings in more than 60% of the participants already on the second day of use of the device. For objective assessment, it is necessary to clarify the diagnosis, for example, endometriosis or polycystic ovary, etc.

In each of examples 3-5, none of the patients revealed any adverse effects that could be associated with the use of the device. Repeated questioning of patients after 2-3 months showed that the duration of the aftereffect after the end of the magnetic therapy session is 30-45 days in 54% of tested persons.

Thus, the claimed device makes it possible to provide targeted magnetic stimulating effect directly on pathogenic areas and organs located at a depth of 3-6 cm from the skin surface, with virtually no effect on tissues located on and near the skin surface, to which a coil of an inductor (applicator) is applied. The shape of the magnetic field of the inductor, made in the form of a bifilar coil, provides an effect on the above areas in order to localize pains of various etiologies.

The main characteristics of the claimed device:
inductor output current effective value −0.01-2.00 A;
oscillator output voltage effective value −1.5-10 V;
oscillation frequency −250-380 kHz;
magnetic field intensity −80-200 µT.

Design features and portability of the device allow one to "deliver" a magnetic signal to the desired area of the human or animal body locally, and, if necessary, affect multiple foci and central processes. Thus, the claimed device is a compact device for magnetic stimulation of general medical purpose, suitable for use in clinical or home conditions for the treatment of menstrual syndrome, hemorrhoids, joint diseases, as well as for the relief of pain of various etiologies, and for healing injuries and stimulating cell proliferation.

The invention claimed is:

1. A device for magnetic effect on living bodies, comprising:
an oscillator and
an inductor connected thereto,
the oscillator operating at a resonant frequency of the inductor,
the inductor comprising a flat bifilar coil having two windings, each winding of the flat bifilar coil comprising an open-circuit winding, said flat bifilar coil comprising a series-oscillatory circuit which is connected to the oscillator, the oscillator providing a sinusoidal shape of an output current at a resonant frequency of the flat bifilar coil,
wherein both open-circuit windings of the flat bifilar coil are coiled into a flat disk, in which wires of the coiled windings are placed on a dielectric substrate and comprise two concentrically arranged spirals from two adjacent wires, one of the spirals being of a wire of one of the coiled windings and a second of the spirals being of a wire of a second of the coiled windings,
wherein an open-circuit terminal of one of the coiled windings is located at an inner end of the one of the coiled windings in a radial direction of the flat bifilar coil, and an open-circuit terminal of the second of the coiled windings is located at an outer end of the second winding in the radial direction of the flat bifilar coil, and other terminals of both coiled windings are connected to corresponding terminals of the oscillator.

2. The device according to claim 1, wherein the inductor and the oscillator are made integral with each other.

3. The device according to claim 1, wherein the wires of the coiled windings of the flat bifilar coil are wound in the same plane tightly to one another, with a total thickness of the windings equal to a diameter of either of said wires.

4. The device according to claim 1, wherein the wires of the coiled windings of the flat bifilar coil are tightly wound one above the other, with a total thickness of the windings equal to two diameters of either of said wires.

5. The device according to claim 1, wherein the oscillator comprises a self-excited oscillator of sinusoidal or square oscillations with an additional coil in a positive current feedback circuit of said self-excited oscillator.

6. The device according to claim 1, wherein the oscillator comprises a self-excited oscillator of sinusoidal oscillations, said self-excited oscillator comprising an additional coil in a positive current feedback circuit of said self-excited oscillator and being adapted for amplitude modulation or manipulation of said oscillations.

7. The device according to claim 1, wherein the oscillator is equipped with an additional circuit of a negative voltage feedback with an ability to control a magnitude of an output voltage and, accordingly, an output current and intensity of a magnetic field generated by the inductor.

8. The device according to claim 1, wherein the oscillator comprises a voltage-controlled oscillator with a phase-locked loop.

9. The device according to claim 1, wherein the resonant frequency of the series-oscillatory circuit of the flat bifilar coil and of the oscillator is set in the range of 250-380 kHz.

* * * * *